(12) United States Patent
Knoff

(10) Patent No.: US 9,406,243 B2
(45) Date of Patent: Aug. 2, 2016

(54) DEVICE AND METHOD FOR TAPERING MEDICATIONS IN POST-OPERATIVE PATIENTS

(71) Applicant: Gillette Children's Specialty Healthcare, St. Paul, MN (US)

(72) Inventor: Celeste Rene Knoff, Cottage Grove, MN (US)

(73) Assignee: GILLETTE CHILDREN'S SPECIALTY HEALTHCARE, St. Paul, MN (US)

(*) Notice: Subject to any disclaimer, the term of this patent is extended or adjusted under 35 U.S.C. 154(b) by 51 days.

(21) Appl. No.: 13/788,590

(22) Filed: Mar. 7, 2013

(65) Prior Publication Data

US 2014/0255892 A1    Sep. 11, 2014

(51) Int. Cl.
*G09B 19/00* (2006.01)
*G06F 19/00* (2011.01)

(52) U.S. Cl.
CPC ............ *G09B 19/00* (2013.01); *G06F 19/3462* (2013.01)

(58) Field of Classification Search
CPC .................... G09F 11/04; G09F 11/23–11/24; A61J 7/04; A61J 7/0409; A61J 7/0472; A61M 15/009; G09B 19/00
USPC .................. 116/308–309, 311–312, 316, 318
See application file for complete search history.

(56) References Cited

U.S. PATENT DOCUMENTS

| 1,211,737 A | 1/1917 | Martini |
| 1,717,060 A | 6/1929 | Mottayaw |
| 2,565,095 A | 8/1951 | Schatzkin |
| 2,587,147 A | 2/1952 | Guion et al. |
| 4,920,912 A | 5/1990 | Kirkling |
| 5,377,614 A | 1/1995 | Glazer |
| 5,468,222 A | 11/1995 | Altchuler |
| 5,554,967 A | 9/1996 | Cook et al. |
| 6,152,067 A * | 11/2000 | Mathison ................ G09F 11/23 116/308 |
| 7,555,995 B1 * | 7/2009 | Stump et al. ................... 116/311 |
| 7,658,162 B2 | 2/2010 | Kreshek |
| 7,661,384 B2 * | 2/2010 | Mataya ................. A61J 1/1412 116/307 |

(Continued)

FOREIGN PATENT DOCUMENTS

| FR | 2771924 A1 | 6/1999 |
| WO | WO 87-03788 | 7/1987 |

OTHER PUBLICATIONS

Rony, R.Y., et al. "Parental Postoperative Pain Management: Attitudes, Assessment, and Management"; Pediatrics: Official Journal of the American Academy of Pediatrics, 125 (e1372); 2010, pp. 1372-1378; DOI: 10.1542/peds.2009-2632. USA.

(Continued)

*Primary Examiner* — Timothy A Musselman
(74) *Attorney, Agent, or Firm* — Barbara A. Wrigley; Fox Rothschild LLP

(57) ABSTRACT

A device and method of tapering medication in a post-operative patient is provided. The system includes a stationary base having indicia thereon representative of a defined period of time; a first circular wheel concentrically positioned on the stationary base, the first circular wheel representative of a first medication being taken by a patient; and a pin coupling the substantially circular wheel to said stationary base to permit the wheel to rotate 360 degrees about said base. The method of tapering medication includes gradually increasing the time intervals that medication is administered to a post-operative patient.

16 Claims, 4 Drawing Sheets

(56) References Cited

U.S. PATENT DOCUMENTS

| | | |
|---|---|---|
| 2007/0056503 A1 | 3/2007 | Sollaccio |
| 2009/0138278 A1 | 5/2009 | Schneider et al. |

OTHER PUBLICATIONS

Vadivelu, N., et al. "Recent Advances in Postoperative Pain Management"; Yale Journal of Biology and Medicine, 83; 2010, pp. 11-25. Pub Med. USA.

Vargas-Schaffer, G. "Is the 'Who' Analgesic Ladder Still Valid?"; Canadian Family Physician, 56; Jun. 2010, pp. 514-517, Canada.

Zhang, C., et al.; "Effects of a Pain Education Program on Nurses' Pain Knowledge, Attitudes and Pain Assessment Practices in China." Journal of Pain & Symptom Management, 36(6); 2008, pp. 616-627; DOI 10.1016/ J/JPAINSYSMMAN.2007.12.020. Elsevier Inc., USA.

Christophersen, E.R., et al.; "Treatments That Work With Children: Empirically Supported Strategies for Managing Childhood Problems," Washington, D.C.: American Psychological Association, 2001, pp. 1-309 (Book). USA.

Corizzo, C. et al.; "Assessment of Patient Satisfaction With Pain Management in Smal Community Inpatient and Outpatient Settings." Oncology Nursing Forum, 27(8), 2000, pp. 1279-1286. USA.

Dowden, S., et al.; "Achieving Organizational Change in Pediatric Pain Management." Pain, Research & Management: The Journal of the Canadian Pain Society, 13(4), 2008, pp. 321-326. Pub Med. Canada.

Gordon, D., et al.; "American Pain Society Recommendations for Improving the Quality of Acute and Cancer Pain Management: American Pain Society Quality of Care Task Force." Archives of Internal Medicine, 165(14), 2005, pp. 1574-1580. USA.

Kavanagh, T., et al.; An Examination of the Factors Enabling the Successful Implementation of Evidence-Based Acute Pain Practices Into Pediatric Nursing. Children'S Health Care, 36(3), 2007, pp. 303-321; DOI: 10.1080/02739610701377970. Canada.

\* cited by examiner

DEVICE AND METHOD FOR TAPERING MEDICATIONS IN POST-OPERATIVE PATIENTS

FIELD OF THE INVENTION

The present invention relates to the administration of medication in post-operative patients and in particular to a device and method for tapering the medication safely and with minimal side effects.

BACKGROUND OF THE INVENTION

Solutions to managing pain are known. However, the management of post-operative pain in children is an art and a science that has yet to be perfected. While research findings differ widely on medications, methods, and timing of interventions to manage post-operative pain, one finding is consistently reported: the treatment of pediatric post-operative pain is suboptimal. Reasons for this deficiency originate in biases of clinicians and parents, difficulties in assessing pain due to variances in physical and developmental levels of children, and lack of research in best practices for pediatric pain management. Because hospital stays are reduced, parents or caregivers must often manage this pain at home. Therefore, educating these primary caregivers in the safe, effective use of pain medications, the reduction of side effects, and the appropriate tapering of the medications is paramount. It is also complex and multifaceted. Preferred methods of patient education are under much scrutiny and the needs of this group of learners are extensive. It is not enough to teach on just the cognitive level. Psychosocial, cultural, and environmental factors impact both the learning and the perceived need for managing children's post-operative pain management at home. Presently, a learning device that addresses these barriers and provides a simple guide for medication management is not available.

While all patients, adult and pediatric, need such a learning device, children are at unique risk for the under treatment of pain because they lack the verbal ability and personal power to demand adequate pain management, and they often do not understand the reason for their suffering. This increased risk poses the single greatest reason for focusing on pain management for this special group of patients. Compounding this risk are the frequent experiences with pain due to the necessity of repeated and ongoing interventions.

The three primary types of pain are nociceptive, inflammatory, and pathological. The post-operative pain generally referred to in this paper is inflammatory pain. Inflammatory pain assists in the healing of the injured body part by creating a situation that discourages physical contact and movement, which reduces further risk of damage and promotes recovery. This type of pain is activated by the immune system and although considered adaptive, reduction in this pain is still vital. Untreated or poorly controlled pain can acutely lead to tachycardia, hypertension, decrease in alveolar ventilation, insomnia, and poor wound healing. Unrelieved acute pain can lead to chronic complications such as chronic pain, sustained changes in central neural functioning, and psychological problems such as heightened pain intensity, anxiety, and post-traumatic stress. In fact it is well known that inadequate treatment of pain contributes to higher rates of complications and lower quality of life and is the most common reason people present for health care. Pain costs society billions of dollars annually, and pain can have a widespread impact on all aspects of life. Despite its recognized significance and the volumes of research dedicated to its management, pain continues to be undertreated especially in children.

As hospital stays following inpatient surgeries become shorter, parents of these children must also learn to manage post-operative pain at home in a shorter period of time. While children are hospitalized, hospital staff use a multimodal approach to pain management employing such techniques as local and regional analgesia, intravenous and intramuscular pain medications, patient controlled analgesia (PCA) techniques, continuous epidural anesthesia and multiple adjunctive agents. Parents at home do not have access to most of these modalities. Therefore, the medications and non-pharmacological techniques for managing post-operative care at home must be used to their utmost effectiveness in order to manage this pain. Because most of these caregivers are not health care professionals, these parents must be taught to be skilled caregivers and knowledgeable pharmacological providers for their children after discharge.

Therefore, what is needed is a device and method that assists post-operative patients and families in the timing, the dosing, and, ultimately, the elimination of pain medications. In particular a simple tool and method are needed that reduce pain and discomfort; maximize health and function; minimize complications and side effects; and allows the patient to taper off medication in a safe manner by assisting in planning pain medication times and in reducing medication usage over time.

BRIEF SUMMARY OF THE INVENTION

The shortcomings of conventional therapies are addressed by the device and method for tapering medications in accordance with the invention.

The novel invention includes the use of a taper wheel that assists post-operative patients and their families in the timing, the dosing, and, ultimately, the elimination of pain medications.

In one aspect of the invention three concentrically placed wheels with indicia thereon are provided.

In another aspect of the invention a 12-hour wheel with three concentrically placed wheels with indicia thereon are provided.

In a further aspect of the invention a writeable base in provided upon which the taper wheel in accordance with the invention is positioned.

In another aspect of the invention a 24-hour taper wheel with two concentrically placed wheels with indicia thereon positioned on a writeable base is provided.

In another aspect of the invention a method for using the taper wheel is provided.

While multiple embodiments, features and advantages are disclosed, still other embodiments of the invention will become apparent to those skilled in the art from the following detailed description taken together with the accompanying figures, the foregoing being illustrative and not restrictive.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION OF THE INVENTION

Figure 1:
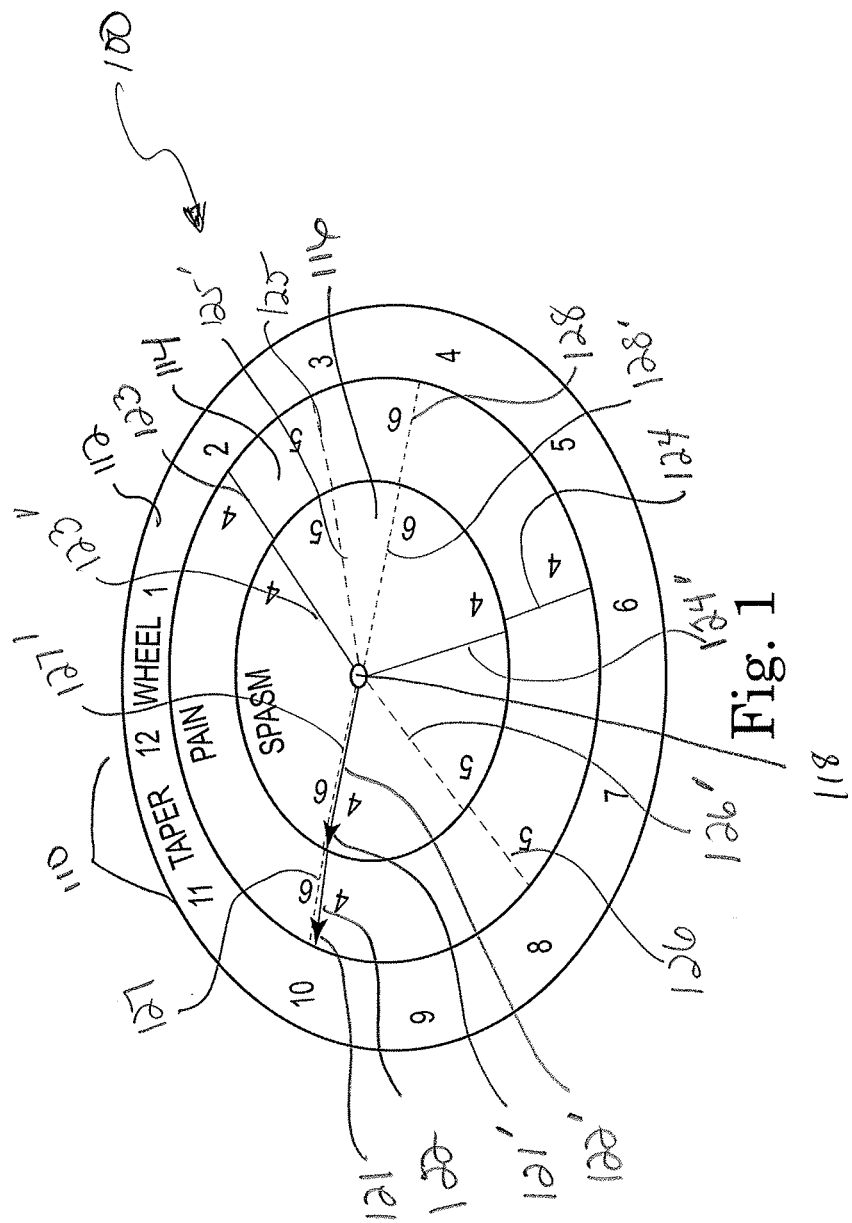
FIG. 1 is a perspective view of a taper wheel in accordance with the invention.

The management of pediatric pain is interdependently complex. Various components such as education, family and provider biases, underlying differences in individual pain, cultural differences, and more are all interwoven into a puzzle that must be sorted and pieced together. A final piece of this puzzle involves the actual pain medications, their dosing, and timing for postoperative pain management at home.

World Health Organization (WHO) guidelines for pain management may be used for acute and chronic pain in any patient that requires analgesics. The WHO standard protocol includes (i) using the oral form of the analgesic; (ii) giving analgesics at regular intervals; (iii) prescribing analgesics according to pain intensity based on pain assessment; (iv) providing analgesic dose based on the individual; and (v) prescribing analgesics with a regularity of administration. Pain management may be improved by recognizing and treating pain promptly (emphasis on comprehensive assessment and the importance of preventive and prompt treatment); involving patients and families in pain management plan (emphasis on customization of care and participation of patient in the treatment plan); improving treatment patterns (eliminate inappropriate practices, provide multimodal therapy); reassessing and adjusting pain management plan as needed (respond not only to pain intensity but to functional status and side effects; and monitoring processes and outcomes of pain management (standardized quality indicators). It is with the foregoing in mind that the present invention was developed.

The present invention may document pain intensity with a numeric or descriptive rating scale and at frequent intervals. Pain may be treated with regularly scheduled analgesics. A multimodal approach is used whenever possible (combinations of techniques). Pain may thus be prevented or controlled to increase function and quality of life. Further, patients should be adequately informed about pain management. Thus, effective patient education is needed.

Dosing guidelines may also be developed to promote the maintenance of therapeutic blood levels of analgesic and the prevention of pain when possible. In other words, scheduled or around-the-clock (ATC) dosing is preferred to pro re nata (PRN) dosing because it has been found to be more effective in reducing pain intensity despite the fact that analgesic quantities may be greater in ATC patients than in PRN patients.

The issue of withdrawal symptoms for any post-operative patient on an opioid or benzodiazepine medication must also be taken into consideration. Withdrawal syndrome is a characteristic pattern of unpleasant signs and symptoms that typically follows abrupt cessation of drugs with central nervous system depressant effects. Predominant characteristics of this syndrome include nervous system hyperirritability, autonomic dysregulation (sneezing, yawning, sweating, tachycardia), gastrointestinal dysfunction, respiratory distress, and abnormal motor movements. Studies have documented withdrawal syndrome in infants and children since the 1980s and symptoms have been seen in patients on as few as five days of ATC opioid and benzodiazepine regimens. There is no current consensus on how opioid and benzodiazepine medications should be discontinued to prevent withdrawal syndrome or how this syndrome should be treated. However, the present inventor has found that a tapering management protocol including the novel taper wheel leads to gradual discontinuation of these medications and lessens withdrawal symptoms.

Typically, patients having had a surgical procedure usually resulting in significant pain and muscle spasms receive adequate pain control during their hospital stay, often with an epidural opioid medication. After a few days, patients are transitioned to oral narcotic medications (oxycodone or percocet) and antispasmotics (valium, vistaril). While this is a complicated medication schedule, it is managed by nurses and most patients report good pain control during their hospital stay. The problem arises when patients are sent home, as they commonly are, on these medications. Current protocol, varies among institutions, but typically consists of providing families with a packet of written papers about the medications, follow-up appointments, physical restrictions, cast care, and dietary and bathing instructions. In addition, the inpatient nurses provide verbal instructions. Given the volume of information and the time limitations of the nurses, it is not difficult to understand why many families have difficulty learning and maintaining this complex medication schedule.

To address these issues, the Taper Wheel and associated method of use was created by the present inventor with the aim of providing effective and safe acute post-operative pain management to children in their homes with the primary goals of reducing pain and discomfort; maximizing health and function; and minimizing complications and side effects. An important secondary goal is tapering off the pain and antispasmodic medications in a safe manner.

Referring now to FIG. 1, a perspective view of a taper wheel 100 in accordance with the invention is illustrated. The taper wheel is a hand-held device that assists in planning medication times and helps to reduce pain medication usage over time. It is especially designed for use with opioid and benzodiazepine medications but those of skill in the art will appreciate that it can be adapted for adults and patients on other types of pain medication. In addition, those of skill in the art will appreciate that taper wheel may include any number of wheels depending on the number of different medications a patient is taking.

Taper wheel 100 broadly includes a stationary base 112, a first medication wheel 114 denominated as a "pain" wheel and a second medication wheel 116 denominated as a "spasm" wheel. For ease of explanation and disclosure this specification will refer to the wheels as "pain" and "spasm" wheels although one of skill in the art will appreciate that the taper wheel in accordance with the invention may include wheels for different medications other than pain and spasm and may include more or fewer wheels than depicted. Such variations are intended to fall within the scope of the present invention. The base wheel 112 is in the form of a clock and includes numerals 1 through 12 representing a twelve hour cycle. Those of skill in the art will appreciate that additional time increments, for example 15 minute or 30 minute increments, may be included on the base wheel 112 without departing from the scope of the invention.

The taper wheel 100 in accordance with the invention includes a stationary substantially round base 112, a concentrically placed inner pain wheel 114 and a concentrically placed outer spasm wheel 116. Those of skill in the art will appreciate that wheels 114 and 116 are designed to individually rotate 360 degrees about a centrally placed pin 118 and stationary round base 112. Pain wheel 114 is used to calculate medication times and dose for pain medications and spasm wheel 116 is used to calculate medication times and doses for spasm medication. The taper wheel depicted in FIG. 1 is designed for calculating medication times and doses within a defined period of time, twelve hours as depicted, with the goal of extending the times of administration gradually. Those of skill in the art will appreciate that pain wheel 114 and spasm wheel 116 may be different colors to clearly distinguish which medication, pain or spasm medication, they represent. In addition, the wheels may be constructed of a whiteboard or other material on which a patient or a caregiver could write nonpermanent markings such as the names of the medications or other information. In this way, the taper wheels are usable. Suitable materials include but not limited to melamine, painted steel or aluminum, laminates, porcelain on steel or aluminum, polyethylene terephthalate (PET) on steel or aluminum and laminated cardstock.

Figure 3:
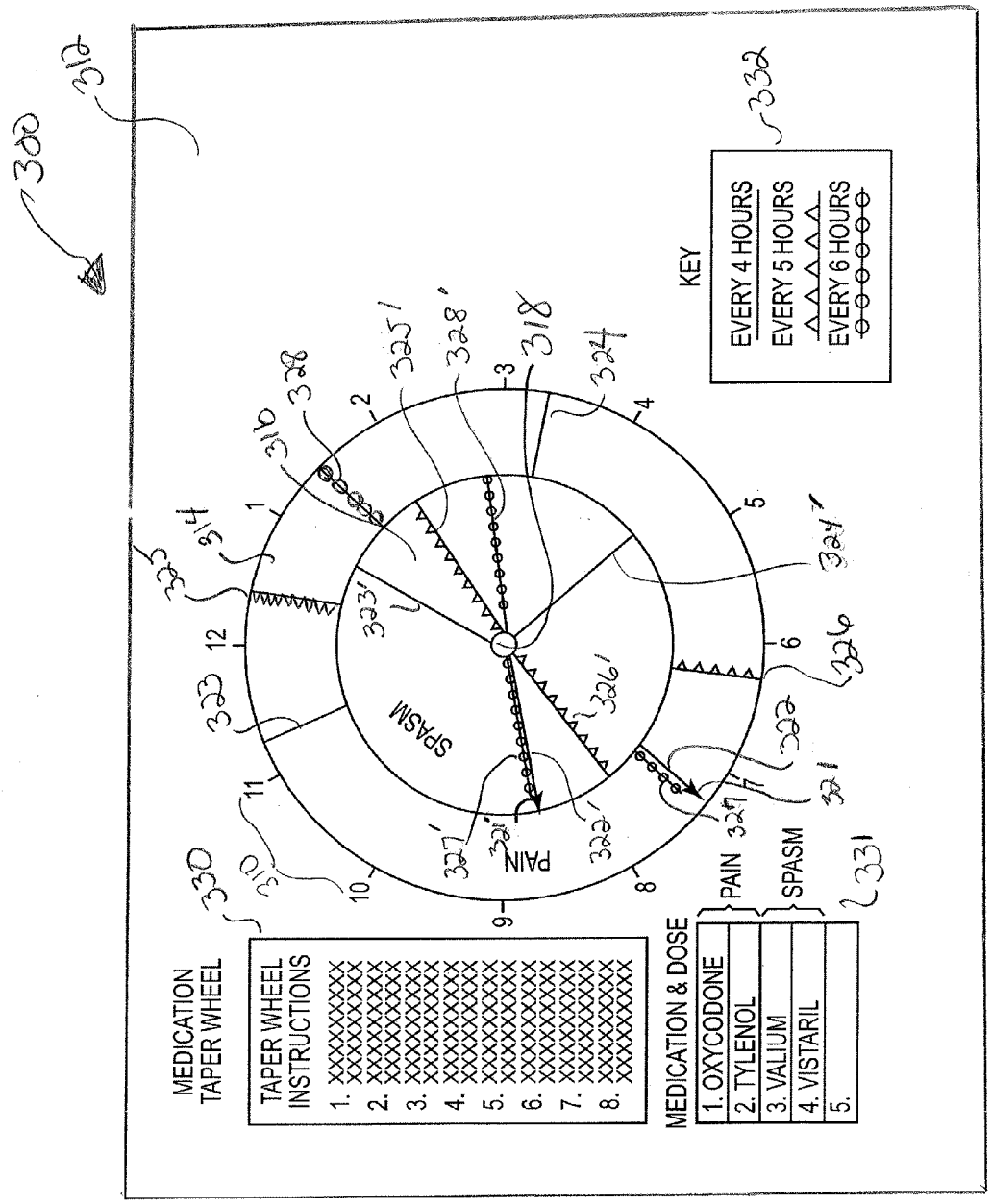
FIG. 3 is a perspective view of a 12-hour taper wheel including instructions on a writeable base.

Referring again to FIG. 1 stationary base 112 includes numerical indicia thereon 110. More specifically, stationary base is in the form of a "clock" having a defined time period of 12-hours with numerals from 1 to 12 indicating the particular hour. Pain wheel 114 may also include indicia thereon, as will hereinafter be described. Pain wheel 114 includes a variety of lines painted or otherwise indicated thereof. The lines represent different time intervals that medications may be given. Because pain and spasm medications are typically given at 4, 5 and 6 hour intervals, three exemplary distinct lines are depicted as 122, 126 and 127 which represent 4 hour, 5 hour and 6 hour intervals, respectively. Lines 122, 126 and 127 may be of different colors or may include different indicia (as best seen in FIG. 3) to distinguish them from each other. Those of skill in the art will appreciate that any number of mechanisms may be used to distinguish between the three lines and still be within the scope of the invention. Those of skill in the art will also appreciate that the taper wheel may be modified to include additional lines representing additional time intervals such as 2 hours, 3 hours, 7 hours, 8 hours and the like without departing from the scope of the invention. In addition, lines representing time intervals other than hourly may be included such as half-hourly, quarterly, etc. Moreover, those of skill in the art will appreciate that medications and similar chemical compounds may be administered to a patient orally, topically or by injection and all forms of administration are intended to be within the scope of the invention.

Arrow 121 is always the "start" for calculating planned medication times. Line 122 represents a four-hour medication cycle and the numeral "4" may be denoted on the left-hand side of line 222 to easily indicate to the caregiver a four-hour medication cycle. Corresponding to line 122 are two additional four-hour interval lines 123, 124 positioned in a four hour and eight hour spaced apart relationship to line 122, respectively.

Second line 125 may be a different color than first line 122 to distinguish between them. The numeral "5" is written on the pain wheel 114 and positioned to the right of the second line to easily indicate to a caregiver a five-hour medication cycle. Corresponding to five-hour line 125 is a second five-hour line 126 in a five hour spaced-apart relationship to line 125 on pain wheel 114.

Third line 127 may be a different color than the first lines 122, 123, 124 or second lines 125, 126 to distinguish among them. The numeral "6" is written on the pain wheel 114 and may be positioned to the left of third line 127 to easily indicate to the caregiver a six-hour medication cycle. Corresponding to third line 127 is one additional six-hour line 128 which is positioned on pain wheel 114 in a six-hour spaced-apart relationship to line 127 on pain wheel 114. Those of skill in the art will appreciate that depending on the medications being administered to a patient, the four-hour, five-hour and six-hour medication cycles for the pain wheel may change and, therefore, are illustrative and not limiting.

Spasm wheel 116 is similar to pain wheel 114. Spasm wheel 116 includes a variety of lines painted or otherwise indicated thereof. The lines represent different time intervals that spasm or other medication may be given to a post-operative patient. Because spasm medications are typically given at 4, 5 and 6 hour intervals, three exemplary distinct lines are depicted as 122', 126' and 127' which represent 4 hour, 5 hour and 6 hour intervals for the administration of spasm medication, respectively. Lines 122', 126' and 127' may be of different colors or may include different indicia (as best seen in FIG. 3) to distinguish them from each other. Those of skill in the art will appreciate that any number of mechanisms may be used to distinguish between the three lines and still be within the scope of the invention. Those of skill in the art will also appreciate that the taper wheel may be modified to include additional lines on the spasm wheel representing additional time intervals such as 2 hours, 3 hours, 7 hours, 8 hours and the like without departing from the scope of the invention. In addition, lines representing time intervals other than hourly may be included such as half-hourly, quarterly, etc.

Arrow 121' is always the "start" for calculating planned spasm medication times. Line 122' includes the numeral "4" denoted on the left-hand side of line 122' to easily indicate to the caregiver a four-hour spasm medication cycle. Corresponding to line 122' are two additional four-hour interval lines 123', 124' positioned in a four hour and eight hour spaced apart relationship to line 122', respectively.

Second line 125' may be a different color than first line 122' to distinguish between them. The numeral "5" is written on the spasm wheel 114' and positioned to the right of the second line to easily indicate to a caregiver a five-hour medication cycle. Corresponding to five-hour line 125' is a second five-hour line 126' in a five hour spaced-apart relationship to line 125' on pain wheel 114'.

Third line 127 may be a different color than the first lines 122, 123, 124 or second lines 125, 126 to distinguish among them. The numeral "6" is written on the pain wheel 114 and may be positioned to the left of third line 127 to easily indicate to the caregiver a six-hour medication cycle. Corresponding to third line 127 is one additional six-hour line 128 which is positioned on pain wheel 114 in a six-hour spaced-apart relationship to line 127 on pain wheel 114.

As with the pain wheel 114 above, those of skill in the art will appreciate that depending on the medications being administered to a patient, the four-hour, five-hour and six-hour medication cycles for the spasm wheel may include additional time periods or fewer time periods and, therefore, are illustrative and not limiting.

Figure 2:
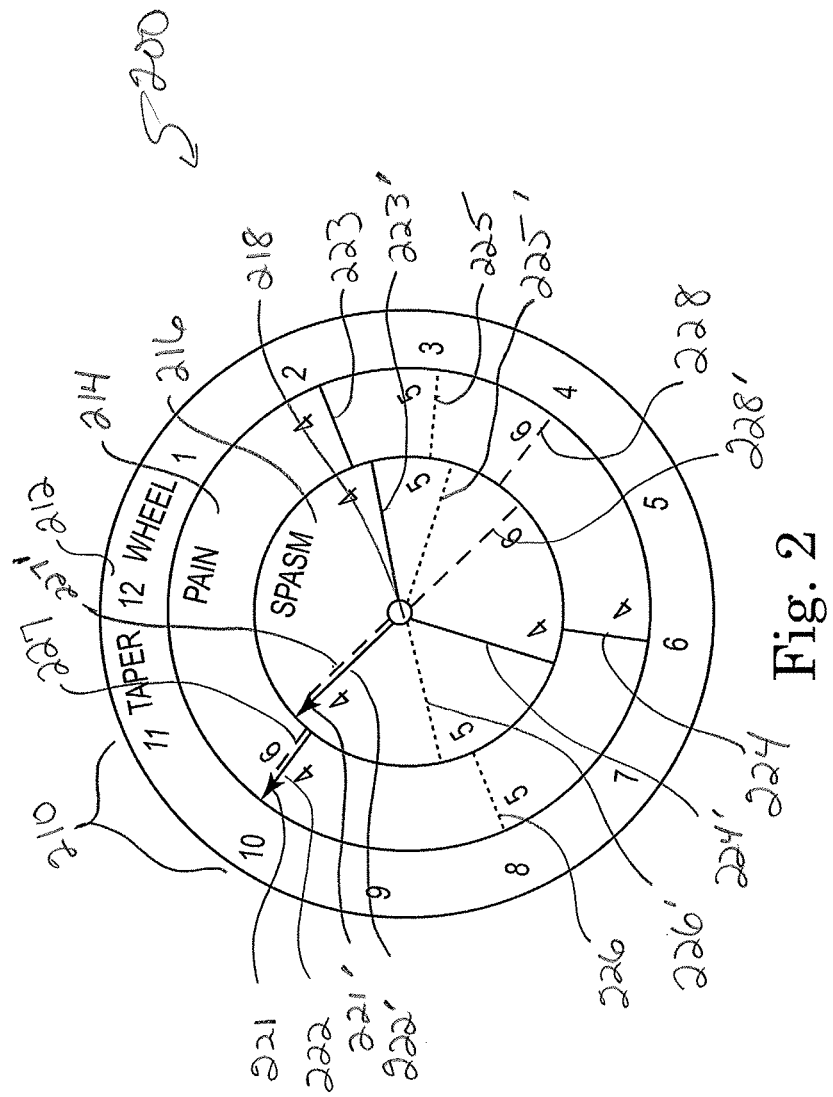
FIG. 2 is a perspective view of a 12-hour taper wheel in accordance with the invention.

Referring now to FIG. 2 an aspect of a taper wheel 200 in accordance with the invention includes a stationary substantially round base 212, a concentrically placed inner pain wheel 214 and a concentrically placed outer spasm wheel 216. Those of skill in the art will appreciate that wheels 214 and 216 are designed to individually rotate 360 degrees about a centrally placed pin 218 and stationary round base 212. Pain wheel 214 is used to calculate medication times and dose for pain medications and spasm wheel 216 is used to calculate medication times and doses for spasm medication. The taper wheel depicted in FIG. 2 is designed for calculating medication times and doses within a defined period of time, twelve hours as depicted, with the goal of extending the times of administration gradually. Those of skill in the art will appreciate that pain wheel 214 and spasm wheel 216 may be different colors to clearly distinguish which medication, pain or spasm medication, they represent. In addition, the wheels may be constructed of a whiteboard or other material on which a patient or a caregiver could write nonpermanent markings such as the names of the medications or other information. In this way, the taper wheels are usable. Suitable materials include but not limited to melamine, painted steel or aluminum, laminates, porcelain on steel or aluminum, polyethylene terephthalate (PET) on steel or aluminum or laminated card stock.

Referring again to FIG. 2 stationary base 212 includes numerical indicia thereon 210. More specifically, stationary base is in the form of a "clock" having a defined time period of 12-hours with numerals from 1 to 12 indicating the particular hour. Pain wheel 214 also includes indicia thereon, as will hereinafter be described. Pain wheel 214 includes a variety of lines painted or otherwise indicated thereof. The lines represent different time intervals that medication may be given. Because pain and spasm medications are typically given at 4, 5 and 6 hour intervals, three exemplary distinct lines are depicted as 222, 226 and 227 which represent 4 hour, 5 hour and 6 hour intervals, respectively. Lines 222, 226 and 227 may be different colors or may include different indicia (as best seen in FIG. 3) to distinguish them from each other. Those of skill in the art will appreciate that any number of mechanisms may be used to distinguish between the three lines and still be within the scope of the invention. Those of skill in the art will also appreciate that the taper wheel may be modified to include additional lines representing additional time intervals such as 2 hours, 3 hours, 7 hours, 8 hours and the like without departing from the scope of the invention. In addition, lines representing time intervals other than hourly may be included such as half-hourly, quarterly, etc.

Arrow 221 is always the "start" for calculating planned medication times. Line 222 includes the numeral "4" denoted on the left-hand side of line 222 to easily indicate to the caregiver a four-hour medication cycle. Corresponding to line 222 are two additional four-hour interval lines 223, 224 positioned in a four hour and eight hour spaced apart relationship to line 222, respectively.

Second line 225 may be a different color than first line 222 to distinguish between them. The numeral "5" is written on the pain wheel 214 and positioned to the right of the second line to easily indicate to a caregiver a five-hour medication cycle. Corresponding to five-hour line 225 is a second five-hour line 226 in a five hour spaced-apart relationship to line 225 on pain wheel 214.

Third line 227 may be a different color than the first lines 222, 223, 224 or second lines 225, 226 to distinguish among them. The numeral "6" is written on the pain wheel 214 and may be positioned to the left of third line 227 to easily indicate to the caregiver a six-hour medication cycle. Corresponding to third line 227 is one additional six-hour line 228 which is positioned on pain wheel 214 in a six-hour spaced-apart relationship to line 227 on pain wheel 214. Those of skill in the art will appreciate that depending on the medications being administered to a patient, the four-hour, five-hour and six-hour medication cycles for the pain wheel may change and, therefore, are illustrative and not limiting.

Spasm wheel 216 is similar to pain wheel 214. Spasm wheel 216 includes a variety of lines painted or otherwise indicated thereof. The lines represent different time intervals that spasm or other medication may be given to a post-operative patient. Because spasm medications are typically given at 4, 5 and 6 hour intervals, three exemplary distinct lines are depicted as 222', 226' and 227' which represent 4 hour, 5 hour and 6 hour intervals for the administration of spasm medication, respectively. Lines 222', 226' and 227' may be of different colors or may include different indicia (as best seen in FIG. 3) to distinguish them from each other. Those of skill in the art will appreciate that any number of mechanisms may be used to distinguish between the three lines and still be within the scope of the invention. Those of skill in the art will also appreciate that the taper wheel may be modified to include additional lines on the spasm wheel representing additional time intervals such as 2 hours, 3 hours, 7 hours, 8 hours and the like without departing from the scope of the invention. In addition, lines representing time intervals other than hourly may be included such as half-hourly, quarterly, etc.

Arrow 221' is always the "start" for calculating planned spasm medication times. Line 222' represents a four hour line and the numeral "4" is denoted on the left-hand side of line 222' to easily indicate to the caregiver a four-hour spasm medication cycle. Corresponding to line 222' are two additional four-hour interval lines 223', 224' positioned in a four hour and eight hour spaced apart relationship to line 222', respectively.

Second line 225' may be a different color than first line 222' to distinguish between them. The numeral "5" is written on the spasm wheel 214' and positioned to the right of the second line to easily indicate to a caregiver a five-hour medication cycle. Corresponding to five-hour line 225' is a second five-hour line 226' in a five hour spaced-apart relationship to line 225' on pain wheel 214'.

Third line 227' may be a different color than the first lines 222', 223', 224' or second lines 225', 226' to distinguish among them. The numeral "6" is written on the spasm wheel 216 and may be positioned to the left of third line 227' to easily indicate to the caregiver a six-hour medication cycle. Corresponding to third line 227' is one additional six-hour line 228' which is positioned on spasm wheel 216 in a six-hour spaced-apart relationship to line 227' on spasm wheel 216.

As with the pain wheel 214 above, those of skill in the art will appreciate that depending on the medications being administered to a patient, the four-hour, five-hour and six-hour medication cycles for the spasm wheel may change and, therefore, are illustrative and not limiting.

Referring now to FIG. 3 another aspect of the taper wheel in accordance with the invention is shown. The taper wheel 300 includes a stationary base 312, and two concentrically placed wheels thereon, a pain wheel 314 and a spasm wheel 316. Pain wheel 314 and spasm wheel 316 are rotatably joined by pin 318 to each other and to base 312. Stationary base 312 may include a variety of information 330 thereon such as instructions for use, medication and dose and/or a key for understanding the lines on the taper wheel 300. Stationary base 312 also includes numerical indicia thereon. More specifically, stationary base 312 includes written indicia in the form of a clock defining a time period of 12-hours with numerals from 1 to 12 and surrounding pain wheel 314.

Pain wheel 314 also includes indicia thereon, as will hereinafter be described. Pain wheel 314 includes a variety of lines painted or otherwise indicated thereof. The lines represent different time intervals that medication may be given. Because pain and spasm medications are typically given at 4, 5 and 6 hour intervals, three exemplary distinct lines are depicted as 322, 326 and 327 which represent 4 hour, 5 hour and 6 hour intervals, respectively, and as indicated in "key" 332. Lines 322, 326 and 327 may be of different colors or may be include different indicia as seen in FIG. 3 to distinguish them from each other. Those of skill in the art will appreciate that any number of mechanisms may be used to distinguish between the three lines and still be within the scope of the invention. Those of skill in the art will also appreciate that the taper wheel may be modified to include additional lines representing additional time intervals such as 2 hours, 3 hours, 7 hours, 8 hours and the like without departing from the scope of the invention. In addition, lines representing time intervals other than hourly may be included such as half-hourly, quarterly, etc.

Arrow 321 is always the "start" for calculating planned medication times. Key 332 indicates that line 322 (and 323, 324) are four hour interval lines for administering medication. Corresponding to line 322 are two additional four-hour interval lines 323, 324 positioned in a four hour and eight hour spaced apart relationship to line 322, respectively.

Second line 325 may be a different color than first line 322 to distinguish between them or may be identified with different indicia as seen in FIG. 3. Key 332 indicates to the caregiver that line 325 identifies a five-hour medication cycle. Corresponding to five-hour line 325 is a second five-hour line 326 in a five hour spaced-apart relationship to line 325 on pain wheel 314.

Third line 327 may be a different color than the first lines 322, 323, 324 and second lines 325, 326 to distinguish among them. As with the four and five hour medication interval lines, key 332 identifies line 327 to the caregiver as a six-hour medication cycle. Corresponding to third line 327 is one additional six-hour line 328 which is positioned on pain wheel 314 in a six-hour spaced-apart relationship to line 327 on pain wheel 314. Those of skill in the art will appreciate that depending on the medications being administered to a patient, the four-hour, five-hour and six-hour medication cycles for the pain wheel may change and, therefore, are illustrative and not limiting.

Spasm wheel 316 is similar to pain wheel 314. Spasm wheel 316 includes a variety of lines painted or otherwise indicated thereof. The lines represent different time intervals that spasm or other medication may be given to a post-operative patient. Because spasm medications are typically given at 4, 5 and 6 hour intervals, three exemplary distinct lines are depicted as 322', 326' and 327' which represent 4 hour, 5 hour and 6 hour intervals for the administration of spasm medication, respectively. Lines 322', 326' and 327' may be of different colors or may be include different indicia as seen in FIG. 3 to distinguish them from each other. Those of skill in the art will appreciate that any number of mechanisms may be used to distinguish between the three lines and still be within the scope of the invention. Those of skill in the art will also appreciate that the taper wheel may be modified to include additional lines on the spasm wheel representing additional time intervals such as 2 hours, 3 hours, 7 hours, 8 hours and the like without departing from the scope of the invention. In addition, lines representing time intervals other than hourly may be included such as half-hourly, quarterly, etc.

Arrow 321' is always the "start" for calculating planned spasm medication times. Key 332 identifies line 322' to the caregiver as a four-hour spasm medication cycle. Corresponding to line 322' are two additional four-hour interval lines 323', 324' positioned in a four hour and eight hour spaced apart relationship to line 322', respectively.

Second line 325' may be a different color than first line 322' to distinguish between them. Key 332 indicates to a caregiver that line 325' represents a five-hour medication cycle. Corresponding to five-hour line 325' is a second five-hour line 326' in a five hour spaced-apart relationship to line 325' on spasm wheel 316'.

Third line 327 may be a different color than the first line 322' to distinguish between them. Once again, key 332 identifies line 327' as a six-hour medication cycle. Corresponding to third line 327' is one additional six-hour line 328' which is positioned on spasm wheel 316 in a six-hour spaced-apart relationship to line 327'.

As with the pain wheel 314 above, those of skill in the art will appreciate that depending on the medications being administered to a patient, the four-hour, five-hour and six-hour medication cycles for the spasm wheel may change and, therefore, are illustrative and not limiting.

Figure 4:
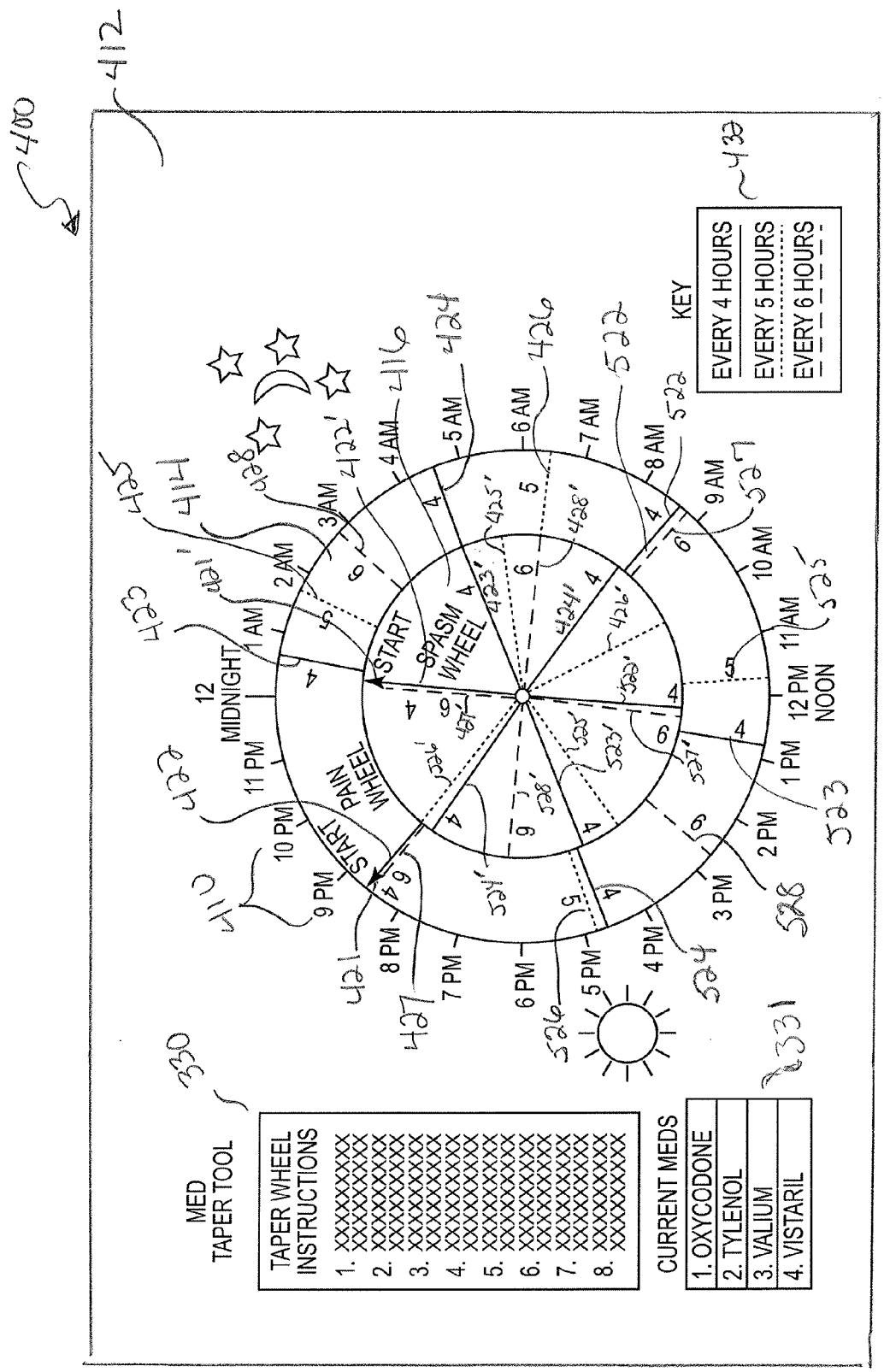
FIG. 4 is a perspective view of a 24-hour taper wheel including instructions on a writeable base.

Referring now to FIG. 4 another aspect of a taper wheel 400 in accordance with the invention is shown. Taper wheel 400 is designed for calculating medication administration times in a 24-hour period with the goal of extending the times of administration gradually thus tapering the patient off the medication.

The taper wheel 400 is substantially similar to the taper wheel 300 of FIG. 3 and includes a stationary base 412, and two concentrically placed wheels, a pain wheel 414 and a spasm wheel 416. Pain wheel 414 and spasm wheel 416 are rotatably joined by pin 418 to each other and to base 412. Stationary base 412 may include a variety of information thereon such as instructions for use 430, current medications 432 and/or a key 432 for understanding the lines on the taper wheel 400. Those of skill in the art will appreciate that base 412 may contain less information or more information. Stationary base 412 also includes numerical indicia thereon corresponding to a twenty-four hour time period with numerals from 1 a.m. to 12 p.m. and from 1 p.m. to 12 a.m. The twenty-four hour numerals surround pain wheel 414. Those of skill in the art will appreciate that the taper wheels 100, 200, 300 of FIGS. 1 through 3 may also be configured as twenty-four hour taper wheels.

Pain wheel 414 also includes indicia thereon, as will hereinafter be described. Pain wheel 414 includes a variety of lines painted or otherwise indicated thereof. The lines represent different time intervals that medication may be given. Because pain and spasm medications are typically given at 4, 5 and 6 hour intervals, three exemplary distinct lines are depicted as 422, 426 and 427 which represent 4 hour, 5 hour and 6 hour intervals, respectively, and as indicated in "key" 432. Lines 422, 426 and 427 may be of different colors or may be include different indicia as seen in FIG. 3 to distinguish them from each other. Those of skill in the art will appreciate that any number of mechanisms may be used to distinguish between the three lines and still be within the scope of the invention. Those of skill in the art will also appreciate that the taper wheel may be modified to include additional lines representing additional time intervals such as 2 hours, 3 hours, 7 hours, 8 hours and the like without departing from the scope of the invention. In addition, lines representing time intervals other than hourly may be included such as half-hourly, quarterly, etc.

Arrow 421 is always the "start" for calculating planned medication times. Key 432 indicates that line 422 (and 423, 424, 522, 523, 524) are four hour interval lines for administering medication. Four-hour interval lines 423, 424, 522, 523 and 524 are positioned in a four hour spaced apart relationship to the preceding four-hour line.

Second line 425 may be a different color than first line 422 to distinguish between them or may be identified with different indicia as seen in FIG. 3. Key 432 indicates to the caregiver that line 425 identifies a five-hour medication cycle. Corresponding to five-hour line 425 are five-hour lines 426, 525 and 526 each in a five hour spaced-apart relationship from the preceding five-hour line on pain wheel 414.

Third line 427 may be a different color than the four hour line series 422, etc. and five-hour line series 425, etc. to distinguish among them. As with the four and five hour medication interval lines, key 432 identifies line 427 to the caregiver as a six-hour medication cycle. Corresponding to third line 427 are additional six-hour lines 428, 527 and 528 which is positioned on pain wheel 414 in a six-hour spaced-apart relationship from the preceding six-hour line on pain wheel 414. Those of skill in the art will appreciate that depending on the medications being administered to a patient, the four-hour, five-hour and six-hour medication cycles for the pain wheel may change to include additional time intervals or fewer time intervals and, therefore, are illustrative and not limiting.

Spasm wheel 416 is similar to pain wheel 414. Spasm wheel 416 includes a variety of lines painted or otherwise indicated thereof. The lines represent different time intervals that spasm or other medication may be given to a post-operative patient. Because spasm medications are typically given at 4, 5 and 6 hour intervals, three exemplary distinct lines are depicted as 422', 426' and 427' which represent 4 hour, 5 hour and 6 hour intervals for the administration of spasm medication, respectively. Lines 422', 426' and 427' may be of different colors or may be include different indicia as seen in FIG. 4 to distinguish them from each other. Those of skill in the art will appreciate that any number of mechanisms may be used to distinguish between the three lines and still be within the scope of the invention. Those of skill in the art will also appreciate that the taper wheel may be modified to include additional lines on the spasm wheel representing additional time intervals such as 2 hours, 3 hours, 7 hours, 8 hours and the like without departing from the scope of the invention. In addition, lines representing time intervals other than hourly may be included such as half-hourly, quarterly, etc.

Arrow 421' is always the "start" for calculating planned spasm medication times. Key 432 identifies line 422' by its pattern to the caregiver as a four-hour spasm medication cycle. Corresponding to line 422' are five additional four-hour interval lines 423', 424', 522', 523' 524' positioned in a four, eight, twelve, sixteen, twenty and twenty-four hour spaced apart relationship to line 422', respectively.

Second line 425' may be a different color than first line 422' to distinguish between them. Key 432 indicates to a caregiver that line 425' represents a five-hour medication cycle. Corresponding to five-hour line 425' are a second five-hour line 426', a third five-hour line 525' and a fourth five hour line 526' in five hour spaced-apart relationships.

Third line 427' may be a different color than lines 422' and 425' to distinguish among them. Once again, key 432 denotes line 427' as a six-hour medication cycle line. Corresponding to third line 427' are three additional six-hour lines 428', 527', 528' which are positioned on spasm wheel 416 in a six-hour spaced-apart relationships.

As with the pain wheel 414 above, those of skill in the art will appreciate that depending on the medications being administered to a patient, the four-hour, five-hour and six-hour medication cycles for the spasm wheel 416 may change and, therefore, are illustrative and not limiting.

To illustrate the use of the taper wheel 200 we refer again to FIG. 2 by way of example. Those of skill in the art will appreciate that the taper wheels illustrated in FIGS. 3 and 4 operate similarly. Arrow 221, 221' is always the starting point, no matter what time interval the administration of medication is desired. The arrow may be red or any color that will easy for a user to readily identify. Arrow 221, 221' is set or moved to the time the patient starts the daily calculation and is often based on the timing of the previous day. The arrow 221, 221' on the pain wheel and/or the spasm wheel is rotated to the desired start time. Assume a pain medication that must be administered every four hours. Therefore, in use an operator first positions arrow 221 at 10:00 a.m. located on base 212 as shown in FIG. 2. This position corresponds to the first planned administration of medication for pain. It can be noted that line 223 is now positioned at 2:00 p.m. which is 4 hours from 10:00 a.m. and that line 224 is positioned at 6 p.m. which is four hours from 2:00 p.m. Continuing in this twelve-hour cycle, and without moving the arrow 221 from its original 10:00 am position, the caregiver can see that the final four hour dose in this twelve-hour cycle is line 222 which is now 10:00 pm. The caregiver can then go around the circle again to obtain the next twelve-hour time period, thus creating a schedule for twenty-four hours. The spasm wheel 216 works similarly to the pain wheel 214 and arrow 221' will be positioned at the time the first administration of medication is planned. Thus, line 222' is positioned at the time the first administration of medication is planned. Lines 223' and 224' will automatically be positioned at the time that is 4 hours away from the previous time that the medication is administered with the first line 222' completing the twelve hour time period. A worksheet may accompany the administration of medication to keep track of the appropriate timing of the medication, the patient's reaction to the medication and the development of any side effects.

Assume now that the caregiver wishes to start tapering the pain and spasm medications by increasing the time interval from a four-hour to a five-hour interval. The arrows 221, 221' are set to the time the pain and spasm medications will first be administered. Referring to FIG. 2 assume this time is 10:00 a.m. As can be noted, lines 225, 225', the five-hour interval lines, are automatically positioned at 3 p.m., which is five hours from the first administration of medication. Similarly, lines 226, 226' automatically lines up to 8:00 p.m., which corresponds to the time that is five hours away from 3:00 p.m. To obtain the next twelve hour cycle, arrow 221, 221' is positioned at 8:00 p.m. Lines 225, 225' and 226, 226' will automatically line up with 1:00 a.m. and 6:00 a.m., respectively.

Assume now that the caregiver wishes to again increase the time interval for administering medication to the patient to 6 hour intervals tapering the amount of medication again. Referring generally to FIG. 2, by way of example, the starting point is always arrow 221, 221'. Assume the caregiver positions arrows 221, 221' on 10:00 a.m., which corresponds to the first time the medication will be taken. As noted lines 228, 228' which represent six-hour interval lines are automatically positioned at 4:00 p.m. Again, without moving arrow 221, 221' from the original 10:00 am position, the caregiver can see that the next 6 hour dose is identified by line 227, 227' at 10:00 pm, thus completing the twelve-hour cycle.

The twenty-four hour taper wheel as best seen in FIG. 4 works similarly to the taper wheel depicted in FIG. 2 except that no additional repositioning of arrow 221, 221' to the next twelve hour cycle is necessary.

Those of skill in the art will appreciate that additional time intervals may be included on the taper wheel in accordance with the invention if a slower withdrawal from medication is desired.

Various modifications and additions may be made to the exemplary embodiments disclosed herein without departing from the scope of the invention. For example, while the embodiments disclosed herein refer to particular features, the scope of this invention also includes embodiments having different combinations of features and embodiments that do not include all of the described features. Accordingly, the scope of the present invention is intended to embrace all such alternative, modifications and variations as fall within the scope of the claims and equivalents thereof.

What is claimed is:

1. A device to assist in the tapering of chemical compounds comprising:
   a stationary base including indicia thereon representative of a defined period of time;
   a first substantially circular wheel concentrically positioned on the stationary base, said first circular wheel corresponding to a first chemical compound taken by a user said first circular wheel including indicia representing a starting point for administration of said first chemical compound and at least a first, second and third four hour lines, said first four hour interval line positioned at the starting point, said second four hour line spaced apart from said first four hour line by a distance representing a four hour interval and said second four hour line spaced apart from said second four hour interval line by a distance representing a four hour interval and said third four hour interval line spaced apart from said second four hour interval line by a distance representing a four hour interval and completing a twelve hour cycle, first and second five hour interval lines said first five hour interval line spaced apart from said starting point by a distance representing a five hour interval and said second five hour interval line spaced apart from said first five hour interval line by a distance representing a five hour interval completing a ten hour cycle;
   a second substantially circular wheel concentrically positioned on said first substantially circular wheel, said second substantially circular wheel corresponding to a second chemical compound being taken by the user said second substantially circular wheel including indicia representing a starting point for administration of said second chemical compound and at least a first, second and third four hour lines, said first four hour interval line positioned at the starting point, said second four hour line spaced apart from said first four hour line by a distance representing a four hour interval and said second four hour line spaced apart from said second four hour interval line by a distance representing a four hour interval and said third four hour interval line spaced apart from said second four hour interval line by a distance representing a four hour interval and completing a twelve hour cycle, first and second five hour interval lines said first five hour interval line spaced apart from said starting point by a distance representing a five hour interval and said second five hour interval line spaced apart from said first five hour interval line by a distance representing a five hour interval completing a ten hour cycle; and
   a pin coupling said second substantially circular wheel to said first substantially circular wheel and said stationary base to permit said first and second wheels to rotate 360 degrees about said base, said interval lines on said first and second substantially circular wheels configured assist in the reduction of said first and second chemical compounds taken by the user by increasing time intervals that said first and second chemical compounds are administered to the user.

2. The device of claim 1 wherein said first, second and third four hour lines include quarterly and half-hourly intervals.

3. The device of claim 1 wherein said base includes additional indicia thereon selected from instructions for use; name of chemical compound; dosage and combination of the foregoing.

4. The device of claim 2 wherein said base includes a key thereon indicating the time interval represented by said line indicia.

5. The device of claim 1 wherein said base or said wheel or both are constructed of a material that can be written on.

6. The device of claim 5 wherein said material comprises whiteboard, melamine, painted steel or aluminum, laminates, porcelain on steel, aluminum, polyethylene terephthalate on steel or polyethylene terephthalate on aluminum.

7. The device of claim 1 wherein said defined period of time is twelve hours.

8. The device of claim 1 wherein said defined period of time is twenty-four hours.

9. The device of claim 1 wherein said first, second and third four hour lines on said first and second substantially circular wheels differ from each other by color, pattern and combinations thereof.

10. The device of claim 1 further comprising a first six hour interval line on said first substantially circular base and a second six hour interval line spaced apart from said first six hour interval line in a six hour increment.

11. The device of claim 1 wherein said first wheel corresponding to a first chemical compound comprises a pain wheel representative of a pain medication.

12. The device of claim 1 wherein said second wheel corresponding to a second chemical compound comprises a spasm wheel representative of a spasm medication.

13. A method of tapering a user from using a chemical compound comprising:
    providing a device to assist in the tapering of a chemical compound by a user, the device having a stationary base including indicia representative of a defined period of time;
    a first substantially circular wheel concentrically positioned on the stationary base, said first circular wheel representative of a first chemical compound being taken the user;
    a pin coupling said at least one substantially circular wheel to said stationary base to permit said wheel to rotate 360 degrees about said base, said first circular wheel including a starting point, first, second and third four hour lines, said first four hour interval line positioned at the starting point, said second four hour line spaced apart from said first four hour line by a distance representing a four hour interval and said second four hour line spaced apart from said second four hour interval line by a distance representing a four hour interval and said third four hour interval line spaced apart from said second four hour interval line by a distance representing a four hour interval and completing a twelve hour cycle, first and second five hour interval lines said first five hour interval line spaced apart from said starting point by a distance representing a five hour interval and said second five hour interval line spaced apart from said first five hour interval line by a distance representing a five hour interval completing a ten hour cycle;
    planning the administration of the chemical compound to the user by rotating the wheel to place the starting point on one of said numerals representing a defined starting time thereby causing said first, second and third four hour interval lines to be spaced apart by a distance representing four, eight and twelve hour intervals;
    administering the chemical compound to the user at said starting time, at said four hour interval, at said eight hour interval and at said twelve hour interval;
    increasing a time period between the administration of the chemical compound by placing a starting point on one of said numerals representative of a defined period of time thereby causing said first five hour interval line to be spaced apart from said starting line by a distance representing a five hour interval and said second five hour interval line spaced apart from said starting line by a distance representing a ten hour interval; and administering the chemical compound to the user at said starting time, at said five hour interval and at said ten hour interval.

14. The method of claim 13 further comprising increasing a time period between the administration of the chemical compound by placing a starting point on one of said indicia representative of a defined period of time thereby causing a first six hour interval line to be spaced apart from said starting point by a distance representing a six hour interval and a second six hour interval line spaced apart from said starting line by a distance representing a twelve hour interval; and administering the chemical compound to the user at said starting time, said six hour interval and said twelve hour interval.

15. The method of claim 13 wherein said indicia representative of a defined period of time are numerals 1 through 12 and said defined period of time is twelve hours.

16. The method of claim 13 wherein said indicia representative of a defined period of time are numerals representing the hours in a twenty-four hour period and said defined period of time is twenty-four hours.

* * * * *